(12) United States Patent
Utz et al.

(10) Patent No.: US 9,636,487 B2
(45) Date of Patent: May 2, 2017

(54) METERS FOR IN-VIVO MONITORING

(75) Inventors: Marcel Utz, Winchester (GB); George T. Gillies, Charlottesville, VA (US); William Broaddus, Midlothian, VA (US); John A. Jane, Charlottesville, VA (US); Matthew R. Begley, Goleta, CA (US)

(73) Assignee: University of Virginia Patent Foundation, Charlottesville, VA (US)

(*) Notice: Subject to any disclaimer, the term of this patent is extended or adjusted under 35 U.S.C. 154(b) by 899 days.

(21) Appl. No.: 13/704,782

(22) PCT Filed: Jun. 17, 2011

(86) PCT No.: PCT/US2011/040976
§ 371 (c)(1),
(2), (4) Date: Jul. 30, 2013

(87) PCT Pub. No.: WO2011/160080
PCT Pub. Date: Dec. 22, 2011

(65) Prior Publication Data
US 2013/0303967 A1    Nov. 14, 2013

Related U.S. Application Data

(60) Provisional application No. 61/355,778, filed on Jun. 17, 2010.

(51) Int. Cl.
*A61M 27/00* (2006.01)
*A61B 5/03* (2006.01)
*A61B 5/00* (2006.01)

(52) U.S. Cl.
CPC .......... *A61M 27/006* (2013.01); *A61B 5/031* (2013.01); *A61B 5/6861* (2013.01);
(Continued)

(58) Field of Classification Search
CPC ..... A61B 5/031; A61B 5/6861; A61B 5/6868; A61B 2562/0247; A61M 27/006; Y10T 29/49117
See application file for complete search history.

(56) References Cited

U.S. PATENT DOCUMENTS 6,077,299 A * 6/2000 Adelberg et al. ............... 623/24
6,358,279 B1 * 3/2002 Tahi et al. ..................... 623/4.1
(Continued)

FOREIGN PATENT DOCUMENTS

WO    WO 2011/160080    12/2011

OTHER PUBLICATIONS

Browd SR, et al., "Failure of cerebrospinal fluid shunts: part II: overdrainage, loculation, and abdominal complications", Pediatr Neurol. 2006; 34:171-6.
(Continued)

*Primary Examiner* — Tatyana Zalukaeva
*Assistant Examiner* — Benjamin Klein
(74) *Attorney, Agent, or Firm* — Robert J. Decker; TannerIP, PLLC

(57) ABSTRACT

Systems and methods for use in monitoring treatment of pressure-related conditions, such as hydrocephalus, include an implantable vessel, and a meter including one or more microfluidic channels connected to the vessel. The microfluidic channels may be configured to detect at least one of pressure and fluid flow rate through the vessel and to be read out remotely by a wirelessly coupled external device. The meter may include a passive resonant (LC) circuit. A dynamic flap may be included in the microfluidic channel that may act as part of the LC circuit. An external device may also be configured to inductively couple remotely to the LC circuit, with-out physical connections to the implantable
(Continued)

vessel or pressure meter, and to display a pressure acting on the pressure meter and/or a fluid flow through the meter.

13 Claims, 8 Drawing Sheets

(52) U.S. Cl.
CPC .... *A61B 5/6868* (2013.01); *A61B 2562/0247* (2013.01); *Y10T 29/49117* (2015.01)

(56) References Cited

U.S. PATENT DOCUMENTS

| | | | |
|---|---|---|---|
| 7,290,454 B2* | 11/2007 | Liu | A61B 5/02152 |
| | | | 73/753 |
| 2006/0235349 A1* | 10/2006 | Osborn et al. | 604/9 |
| 2007/0105339 A1* | 5/2007 | Faris | 438/455 |
| 2009/0112103 A1* | 4/2009 | Kassem | 600/488 |
| 2010/0022896 A1* | 1/2010 | Yadav et al. | 600/488 |
| 2010/0241241 A1* | 9/2010 | McKnight | A61F 2/04 |
| | | | 623/23.68 |

OTHER PUBLICATIONS

Rocque BG, et al., "Ventricular shunt tap as a predictor of proximal shunt malfunction in children: a prospective study", J Neurosurg Pediatr, 2006; 1:439-43.
Drake JM, et al. "CSF shunts 50 years on—past, present and future" Childs Nerv Syst. 16:800-4.
The International Search Report corresponding to the PCT/US2011/040976 application.
U.S. Appl. No. 61/355,778, filed Jun. 17, 2010.

* cited by examiner

METERS FOR IN-VIVO MONITORING

CROSS-REFERENCES TO RELATED APPLICATIONS

The present application is a national stage application of, and claims priority to, International Application No. PCT/US2011/040976 filed Jun. 17, 2011, which claims the benefit under 35 U.S.C. §119(e) of provisional application Ser. No. 61/355,778 filed Jun. 17, 2010, the contents of which are hereby incorporated herein by reference in their entireties.

BACKGROUND OF THE INVENTION

Hydrocephalus commonly results from an imbalance between CSF production within the brain and re-absorption of CSF into the vascular space. Problems of impaired CSF re-absorption are most common in infants related to perinatal intracranial bleeding and in elderly individuals with slowly progressive impairment of CSF re-absorption ("normal pressure hydrocephalus"). Another cause can be impairment of flow of CSF through the brain's ventricular system (obstructive hydrocephalus). It is estimated that almost 200,000 individuals are diagnosed with hydrocephalus each year in the US. An additional group of patients develop obstructive hydrocephalus due to tumors or other pathologies affecting CSF flow in the brain.

The majority of shunts drain CSF by way of a catheter extending from the lateral cerebral ventricle through brain parenchyma, and a burr hole in the skull, to the sub-galeal space beneath the scalp. A pressure-controlled flow valve is connected to this catheter, and the outlet is connected in turn to a distal catheter that drains into a space capable of re-absorbing CSF, such as the peritoneal space in the abdomen. Placement of a shunt is accomplished by way of incisions over the burr-hole site on the scalp and the distal catheter placement site (abdomen, chest or neck). After connecting the ventricular and distal catheters to the valve, the incisions are sutured, leaving the entire system beneath the skin surface. Placement of a shunt is always carried out under controlled sterile conditions, and any repairs or changes of components require additional procedures in the operating room.

Shunt malfunctions can be considered in terms of providing inadequate or excessive CSF drainage. Browd S R, Gottfried O N, Ragel B T, Kestle J R., "Failure of cerebrospinal fluid shunts: part II: overdrainage, loculation, and abdominal complications", Pediatr Neurol. 2006; 34:171-6. The most common malfunctions result in complete or intermittent blockage of CSF flow. Clinical techniques for determining whether a shunt is blocked or malfunctioning are the subject of considerable discussion (Browd et al., 2006). This is primarily because no external means of gauging shunt functioning has been available. The technique of choice involves placement of a needle through the scalp into a bulb-shaped reservoir that is typically built into the valve housing upstream of the valve mechanism ("shunt tap" procedure). However, this approach is not generally reliable and carries a risk of shunt infection, which are virtually impossible to eradicate without replacing the shunt surgically. Rocque B G, Lapsiwala S, Iskandar B J, "Ventricular shunt tap as a predictor of proximal shunt malfunction in children: a prospective study", J Neurosurg Pediatr. 2006; 1:439-43. The only other alternative, exposing a valve surgically to ascertain its function, would require a trip to the operating room, typically under general anesthesia.

One of the main ways that shunt malfunctions are diagnosed is the development of recurrent symptoms of hydrocephalus. Given that the earliest signs of shunt malfunction are often severe headaches, somnolence or cognitive impairment, it can be appreciated that simple ways to establish whether a shunt is patent and to determine the patient's intracranial pressure would be of great value.

Cerebrospinal fluid (CSF) shunts have revolutionized the treatment and outcomes for hydrocephalus since their invention almost 60 years ago. Drake J M, Kestle J R, Tuli S., "CSF shunts 50 years on—past, present and future" Childs Nerv Syst. 2000; 16:800-4. While these relatively simple devices have been effective in treating hydrocephalus, they are prone to failure, infection and other complications, leading to a recent panel recommendation for improved shunt technologies (NIH Proceedings 2005) and a recent NIH Program Announcement promoting grant applications to develop promising new technologies (NIH Program Announcement PA-09-205).

A particular problem lies in the fact that once implanted, the only indication of implant failure is the recurrence of clinical symptoms. Implanted shunt valves to drain CSF constitute a key element in the therapy of various forms of hydrocephalus. However, the implanted devices are prone to blockage. Currently, the only indication of shunt malfunction is the recurrence of clinical symptoms.

BRIEF SUMMARY OF THE INVENTION

The present invention provides systems and methods which may be useful for monitoring internal pressure and/or flow-related conditions, such as hydrocephalus.

As indicated above, one problem with implantable shunts, and other vessels, is the limited ability to detect and/or predict failure of the implanted device before physiological symptoms result. Similar problems may be present in other pressure-related conditions and treatments such as, for example, those involving external ventricular drainage systems (EVDs), which are currently used for monitoring and treating elevated intracranial pressure (e.g., due to trauma, brain tumors, stroke) and hydrocephalus in the intensive care setting, and elevated (or decreased) intracranial pressure in a variety of neurological pathologies. Pathways to monitor the operation of shunts in-vivo, giving an indication of implant failure before symptoms recur, is an exemplary and non-limiting aspect and object of an embodiment of the present invention. However, applicability of the invention is envisioned in other contexts, such as where an implantable, remotely-readable, meter may be used in fluid communication with a catheter extending outside of the body, or a reservoir exposed to an internal fluid pressure within the body.

An aspect of an embodiment of the present invention comprises, but is not limited thereto, the development of implantable microfluidic pressure sensors, that may work in conjunction with existing shunt technology, that allow non-invasive measurement of the flow rate and pressure drop across the shunt valve. The present subject matter may also find applicability in the monitoring of other implantable vessels, such as catheters, reservoirs, etc., in other parts of the body and for other pressure- and flow-related symptoms, pathologies and/or treatments, e.g. arterial shunts for dialysis, vascular stents, ureteral or biliary stents, intrahepatic portosystemic shunts or splenorenal shunts.

An aspect of an embodiment of the present invention may include, but not be limited to, the integration of microfluidic flow meters into cerebrospinal fluid (CSF) shunt catheters that will allow non-invasive, in-vivo monitoring of shunt function through in-situ measurement of pressure and/or flow.

According to aspects of the invention, non-invasive methods to confirm and quantify the function of CSF shunts may be provided, for example, that allow continued monitoring of CSF drainage in hydrocephalus patients without the need for surgical intervention. Exemplary microfluidic pressure and/or flow sensors may rely on pressure-induced deformation of compliant features, which alter the spectrum of radiofrequency resonators. These changes may be detected by inductive, touch-less coupling to a hand-held measurement device through the skin.

Exemplary pressure/flow meters may also be incorporated into or added to external ventricular drainage systems (EVDs) used for monitoring and treating elevated intracranial pressure (e.g., due to trauma, brain tumors, stroke) and hydrocephalus in the intensive care setting.

Further embodiments may be configured as a fully implantable ventricular reservoir with a pressure monitor allowing subsequent non-invasive continuous monitoring of intracranial, or other, pressure to be used in managing elevated (or decreased) intracranial pressure in a variety of neurological pathologies, or other pressure and/or flow-related conditions.

According to first aspects of the invention, an apparatus for use in monitoring treatment of conditions such as hydrocephalus, may include an implantable shunt; and a meter including one or more microfluidic channels connected to the shunt and configured to detect at least one of pressure and fluid flow rate through the shunt and to be read out remotely by a wirelessly coupled external device. In embodiments, the meter may include a passive resonant tank (LC) circuit.

In embodiments, the microfluidic channel may include at least one volumetric reservoir. Embodiments may include a plurality of reservoirs, each of the plurality of reservoirs having different dimensions and configured as separate LC circuits.

In embodiments, the meter may include a dynamic (e.g. moveable, pliable or deformable) layer in communication with the at least one reservoir and a static layer opposite the dynamic layer, the static layer including an inductor coil configured to react to movement of the dynamic layer.

In embodiments, the microfluidic channel may include at least one dynamic (e.g. moveable, deformable, pliable) flap at least partially obstructing the microfluidic channel, and the meter may be configured such that a displacement (e.g. movement, flexure, deformation, etc.) of the flap changes or modulates a capacitance of a capacitor of the LC circuit. In embodiments, the flap may include a low-dielectric material. In embodiments, the flap may include a membrane of Polydimethylsiloxane (PDMS).

Embodiments may include an external device configured to inductively couple remotely to an implantable device such as those described herein, e.g. with an LC circuit, without physical connections (such as leads or wires), and to display a pressure acting on, or a flow rate of a fluid passing through, the meter. In embodiments, the external device may be configured for wearing by the patient such that the external device may maintain a prolonged and/or intermittent coupling and/or communication with the implantable device. For example, the external device may be configured in and/or mounted to a headgear or other device suitable for wearing by the patient. In embodiments, the external device may include a wireless communication device configured to transmit pressure and/or flow information received from the implantable device.

In embodiments, the implantable shunt and meter may be included in a fully implantable unit. Embodiments may further include a control circuit in the implantable unit and configured to process data from the meter; and/or a memory device included in the implantable unit and configured to store and retrieve the processed data from the control circuit. In embodiments, the control circuit may be further configured to communicate the stored data when interrogated by an external device, at predetermined intervals, based on predetermined conditions, etc.

According to further aspects of the invention, an apparatus for use in monitoring fluid pressure within a body may include an implantable vessel (e.g. a reservoir, shunt or catheter component); and a pressure meter including one or more microfluidic channels connected to the vessel and configured to detect a pressure at the vessel and to be read out remotely by a wirelessly coupled external device.

In embodiments, the vessel and the pressure meter may be included in an implantable unit. Embodiments may further include a control circuit included in the implantable unit and configured to process data from the pressure meter; and/or a memory device included in the implantable unit and configured to store and retrieve the processed data from the control circuit. In embodiments, the control circuit may be further configured to communicate the stored data when interrogated by an external device, at predetermined intervals, based on predetermined conditions, etc.

In embodiments, a rechargeable power source may be included in the implantable unit and configured to recharge electrical battery power via inductive coupling with a wirelessly coupled external device.

In embodiments, the pressure meter may include a passive resonant tank (LC) circuit.

In embodiments, the microfluidic channel may include at least one volumetric reservoir. In embodiments, the microfluidic channel may include a plurality of reservoirs, each of the plurality of reservoirs having different dimensions and configured as separate LC circuits.

In embodiments, the pressure meter may include a dynamic (e.g. moveable, pliable or deformable) layer in communication with the at least one reservoir and a static layer opposite the dynamic layer, the static layer including an inductor coil configured to react to displacement (e.g. movement, flexure, deformation, etc.) of the dynamic layer.

In embodiments, the microfluidic channel may include at least one dynamic (moveable, deformable, pliable) flap at least partially obstructing the microfluidic channel, and the pressure meter may be configured such that a displacement (e.g. movement, flexure, deformation, etc.) of the flap changes or modulates a capacitance of a capacitor of the LC circuit.

Embodiments may include an external device configured to inductively couple remotely to the LC circuit, without physical connections (such as leads or wires) to the implantable vessel or pressure meter, and to display a pressure acting on the pressure meter. In embodiments, the external device may be configured for wearing by the patient such that the external device may maintain a prolonged and/or intermittent coupling and/or communication with the implantable device. For example, the external device may be configured in and/or mounted to a headgear or other device suitable for wearing by the patient. In embodiments, the external device may include a wireless communication device configured to transmit pressure and/or flow information received from the implantable device.

According to further aspects of the invention, exemplary methods of monitoring the treatment of pressure-related conditions, such as hydrocephalus etc., may include one or more steps of implanting a vessel (e.g. a shunt, a catheter, a reservoir, etc.) and a connected meter with a microfluidic channel into a patient; detecting at least one of a pressure acting on, and a flow rate of a fluid through, the vessel via an LC circuit included in the flow meter; and communicating information regarding the detected pressure and/or flow rate to an external device via inductive coupling and without physical connection of the external device to the vessel or the flow meter.

In embodiments, the microfluidic channel may include at least one volumetric reservoir. In embodiments, the meter may include a plurality of volumetric reservoirs, each of the plurality of reservoirs having different dimensions and configured as separately readable LC circuits.

In embodiments, the meter may include a dynamic (e.g. moveable, pliable or deformable) layer in communication with the at least one reservoir and a static layer opposite the dynamic layer, the static layer including an inductor coil configured to react to displacement (e.g. movement, flexure, deformation, etc.) of the dynamic layer.

In embodiments, the microfluidic channel may include at least one dynamic (e.g. moveable, pliable or deformable) flap at least partially obstructing the microfluidic channel, and the meter may be configured such that a displacement (e.g. movement, flexure, deformation, etc.) of the flap changes a capacitance of a capacitor of the LC circuit.

According to further aspects of the invention, exemplary methods of manufacturing a meter may include one or more steps of patterning a microfluidic channel into a substrate; and providing an LC circuit proximate to the microfluidic channel that is configured to detect at least one of a pressure within and a fluid flow through the microfluidic channel.

Embodiments may further include one or more steps of providing at least one volumetric reservoir in communication with the microfluidic channel; at least partially covering the at least one reservoir with a dynamic (e.g. pliable or deformable) layer; and providing a static layer opposite the dynamic layer, the static layer including an inductor coil configured to react to flexure or movement of the dynamic layer.

In embodiments, the inductor coil may be micro-patterned onto the static layer.

Embodiments may include one or more steps of forming a plurality of volumetric reservoirs, each of the plurality of reservoirs having different dimensions and configured as separately readable LC circuits.

Embodiments may include one or more steps of providing at least one dynamic (e.g. moveable, pliable or deformable) flap at least partially obstructing the microfluidic channel, and configuring the meter such that a displacement (e.g. movement, flexure, deformation, etc.) of the flap changes a capacitance of a capacitor of the LC circuit. In embodiments, the at least one flap may include a low-dielectric material, and/or may include a membrane of PDMS.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention claimed. The detailed description and the specific examples, however, indicate only preferred embodiments of the invention. Various changes and modifications within the spirit and scope of the invention will become apparent to those skilled in the art from this detailed description.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and various ways in which it may be practiced. In the drawings.

DETAILED DESCRIPTION OF THE INVENTION

Figure 1:
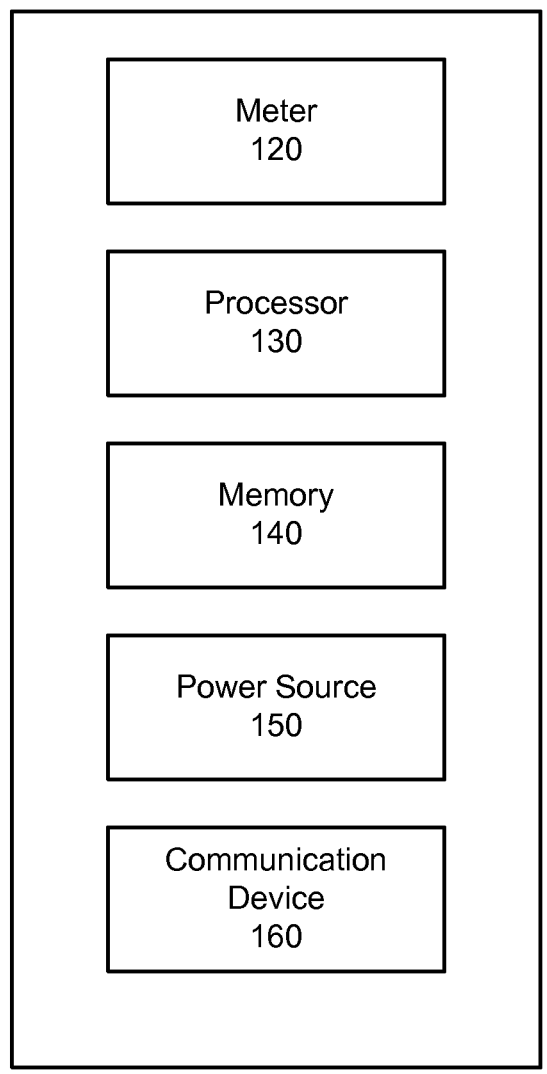
FIG. 1 is a block schematic illustration of a first embodiment of an exemplary implantable device according to aspects of the invention.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It also is be noted that as used herein and in the appended claims, the singular forms "a," "an," and "the" include the plural reference unless the context clearly dictates otherwise. Thus, for example, a reference to "a reservoir" is a reference to one or more reservoirs and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals reference similar parts throughout the several views of the drawings.

Moreover, provided immediately below is a "Definition" section, where certain terms relating to the invention are defined specifically. Particular methods, devices, and materials are described, although any methods and materials similar or equivalent to those described herein can be used in the practice or testing of the invention. All references referred to herein are incorporated by reference herein in their entirety.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage.

The term "patient" as in treatment of "a patient" refers to a mammalian individual afflicted with or prone to a condition, disease or disorder as specified herein, and includes both humans and animals.

The term "dynamic" as used herein refers to walls, covers, layers, flaps, and other structural components of devices described herein that are intended to be moveable with respect to other device components, pliable and/or deformable under normal operating conditions.

The term "vessel" as used herein refers to various structural components of devices described herein in which a fluid can flow or be contained, such as catheters, shunts, reservoirs, etc.

The term "fully implantable" as used herein refers to devices that are configured to be implanted in a patient's body without components, attachments or physical leads, such as wires, tubes or other connections, extending outside of the body.

The following preferred embodiments may be described in the context of exemplary CSF shunt procedures for ease of description and understanding. However, the invention is not limited to the specifically described devices and methods, and may be adapted to various clinical applications without departing from the overall scope of the invention. For example, devices and related methods including concepts described herein may be used for various treatment and monitoring methods involving pressure and/or flow-related conditions.

As shown in FIG. 1, a first embodiment of the invention may include an implantable device 100 with one or more of a meter 120, a processor 130, a memory 140, a power source 150, and/or communication device 160. Implantable device 100 may include one or more connections, ports, etc., for joining the device to, and providing fluid communication with, vessels such as shunts, catheters, or other reservoirs that are fully or partially implanted in a patient's body. The connections may include one or more input and/or output ports. The meter 120 may take various forms, such as those described further herein, and may include, for example, one or more remotely or otherwise controllable valves, one or more microchannels and a pressure and/or flow sensor that is remotely readable by wirelessly coupling the device 100 with an external device.

The processor 130 may be configured to process various data detected by the meter 120 and/or to store raw and/or processed data in memory 140, or communicate raw, processed and/or stored data to an external device via communication device 160. Memory 140 may include various electronic storage means, and may be configured to store various programming instructions to be used by the processor 103, for example, to interpret detected data, calibrate the device 100, force an inductance to push on a capacitor sensor, configure the device to report intermittent readings, respond to remote interrogation, etc. Power source 150 may include various electrical power sources, such as rechargeable batteries and associated circuitry configured to be remotely chargeable by, for example, wirelessly coupling the device 100 with an external charger.

In embodiments, an implantable device, such as device 100, may be remotely controllable and/or programmable via an external device. For example, communication device 160 may be configured to receive commands, e.g. to adjust flow metering, to stop or start a fluid flow, etc., and/or programming updates from an external device and to apply them to instructions in memory 140. The device 100 may also be configured to perform predetermined actions at scheduled intervals, in response to detected pressure and/or flow conditions, etc. For example, valves in meter 120 may be controlled on a predetermined schedule to regulate flow through the meter, throttle, open and/or shut the meter according to detected pressure, etc.

Figure 2:
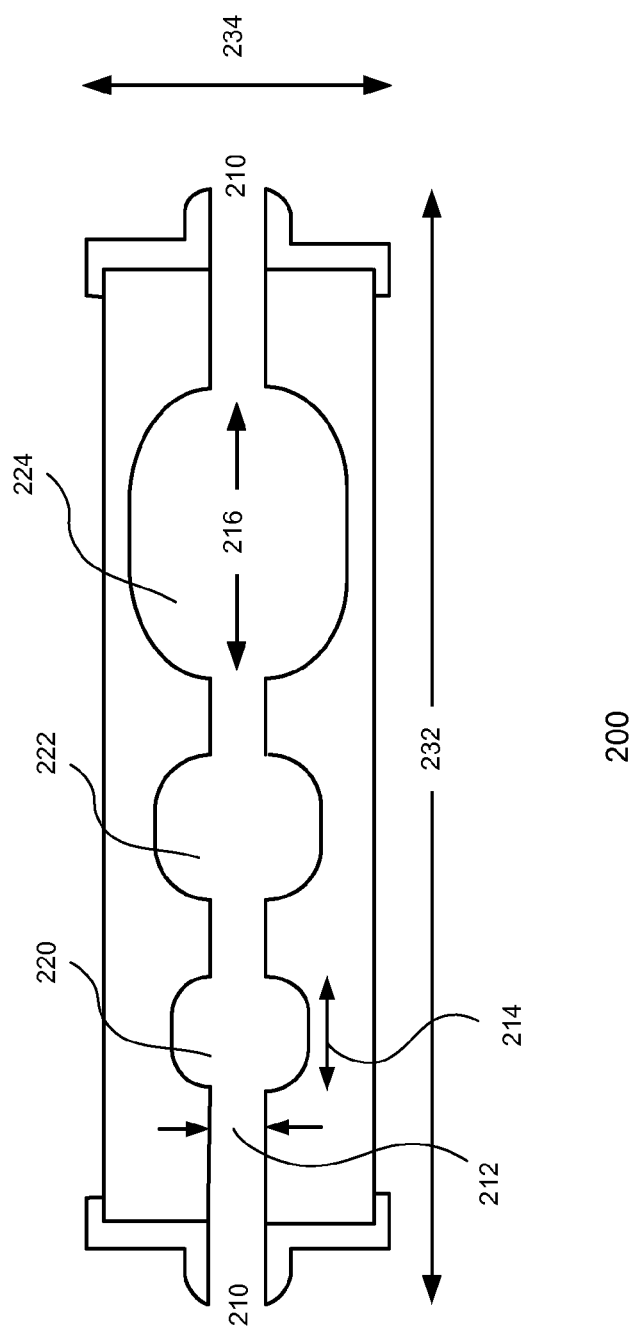
FIG. 2 is a cutaway top view of an exemplary implantable meter including a plurality of reservoirs according to aspects of the invention.

FIG. 2 provides additional details of an exemplary meter according to aspects of the invention including a plurality of reservoirs. As shown in FIG. 2, meter 200 may include ports 210 for connection with a vessel. Ports 210 may include remotely or otherwise controllable valves, and may be in communication with a microchannel 212 with an interior diameter of, for example, approximately 1 mm. Microchannel 212 may be fabricated, for example, on a substrate using micromachining techniques.

A plurality of reservoirs 220, 222 and 224 may be in communication with the microchannel 212. It should also be noted that, embodiments of the invention may also include only one reservoir, or other numbers of reservoirs than shown in FIG. 2. In the embodiment shown in FIG. 2, the reservoirs 220, 222 and 224 include different interior dimensions, and volumes, which may be used in processing techniques that determine a pressure, and fluid flow, through the meter. In embodiments, the interior diameters of the reservoirs may vary, for example, between approximately 1 mm to approximately 5 mm. For example, reservoir 220 may have an interior diameter 214 of between approximately 1 mm to 2 mm, reservoir 224 may have an interior diameter 216 of approximately 5 mm, and reservoir 222 may have an interior diameter between approximately 2 mm to 4 mm.

Meter 200 may have, for example, a length 232 of approximately 10 mm to 15 mm and a width 234 of approximately 3 mm to 4 mm. Additional details of a cutaway side view of exemplary meter 200 are shown in FIG. 3.

Figure 3:
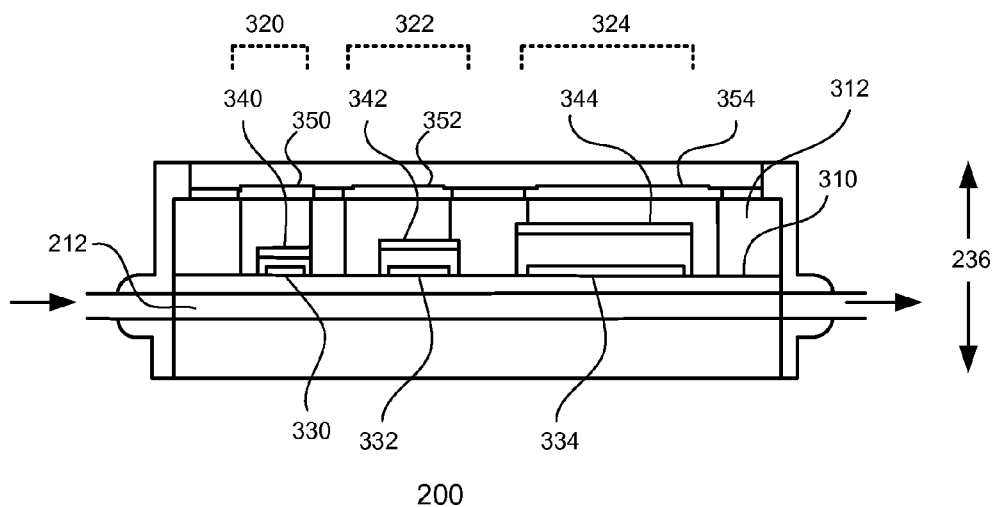
FIG. 3 is a cutaway side view showing additional details of an exemplary implantable meter according to aspects of the invention.

As shown in FIG. 3, the meter 200 may have a height 236 of approximately 2 mm to 4 mm and may include a dynamic layer 310 that is locally deformable subject to fluid pressure within the microchannel 212. A plurality of LC circuits 320, 322 and 324 may be disposed with respect to each of the reservoirs 220, 222, and 224 shown in FIG. 2. Dynamic capacitor plates 330, 332, and 334, corresponding to each of the LC circuits, may be disposed on the dynamic layer 310. Static capacitor plates 340, 342, 344 may be disposed, e.g. by depositing metal into recessions in a patterned top substrate 312, above each of dynamic capacitor plates 330, 332, and 334, respectively. Inductor coils 350, 352 and 354 may be disposed above each set of dynamic and static capacitor plates, with electrical connections to the respective capacitor plates fabricated through the substrate 312. Thus, each group of dynamic capacitor plate, static capacitor plate and inductor coil may form an LC circuit responsive to pressure in corresponding reservoirs and/or regions of the microchannel 212. A isometric view of an exemplary LC circuit is shown in FIG. 4.

Figure 4:
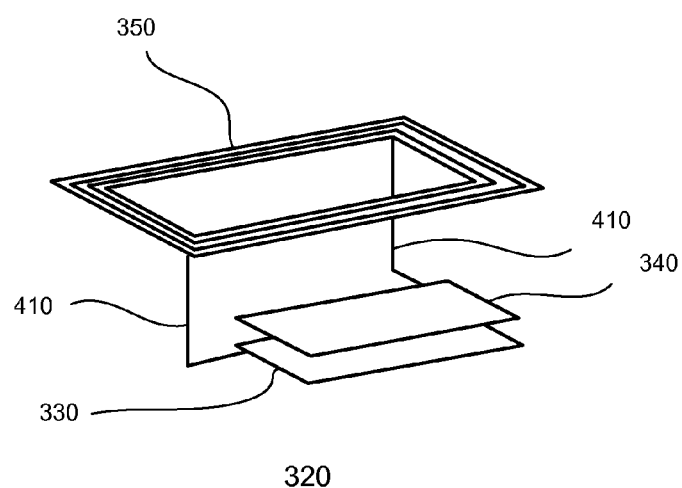
FIG. 4 is an illustration showing additional details of an exemplary LC circuit according to aspects of the invention.

As shown in FIG. 4, exemplary LC circuit 320 may include dynamic capacitor plate 330, static capacitor plate 340 and inductor coil 350, interconnects 410.

As mentioned above, the meter 200 may be fabricated using micro-machining techniques to achieve small feature sizes. A microfluidic channel, such as microchannel 212, may be patterned into a substrate (e.g. PMMA or glass) via photolithography, etching etc., and capped with a deformable elastomer layer, such as dynamic layer 310. A metal may then patterned on the elastomer over the channel, and/or reservoirs of the channel. This creates a bottom (dynamic) capacitor plate whose vertical position is a function of internal fluid pressure. The top (static) capacitor plate may be created by depositing metal into recessions in a patterned top substrate. Finally, the inductor may be micro patterned onto the very top of the top substrate. Connections between the inductor and capacitor plates may be made by drilling small vias through the top substrate and electroplating interconnects.

Thus, according to aspects of the invention, a fluid may be introduced to, and/or flow through, a microfluidic channel, such as which has several reservoirs that are capped by a deformable film. The deformable film may include one-half of a capacitor, such that the capacitance changes with pressure in the reservoir. By measuring pressure at sequential locations along the microchannel, flow rates can be extracted using conventional flow mechanics, e.g. by considering pressure differentials and resistance between the reservoirs. The dynamic range of the flow meter can be extended by using multiple reservoirs (i.e. capacitors), each with dimensions tailored to specific pressure ranges and flow rates.

According to further aspects of the invention, exemplary systems and methods may be used to quantify relatively small flow rates and low back pressures, using an implanted (in-vivo) device that provides flow information without outside physical tethers. Embodiments of the invention may detect pressures in a range of, for example, cm $H_2O$ to 20 cm $H_2O$ (roughly 2 to 14 mm Hg), at a flow rate resolution of approximately 1 µl/s.

In embodiments, each reservoir may be configured as an independently functioning and readable LC circuit. Multiple reservoirs may also facilitate remote read-out of the device. That is, for example, a proper positioning of the remote detector over the flow meter may be determined by maximizing the signals from a plurality of LC circuits.

Deformation of dynamic layers, flaps and the like, in exemplary implanted meters may affect the capacitance of an integrated radio frequency resonator, shifting its resonance frequency. The pressure values can then be interrogated non-invasively by an external measurement device that couples to the resonators inductively across the skin. Flow may be quantified from a pressure drop across the meter or across a shunt valve or other vessel. The measurement device may be used, for example, by a clinician or nurse during check-up visits, or by the patient such as in an extended home-use environment. The use of an implanted meter and an external remote reading device is shown in FIG. 5.

Figure 5:
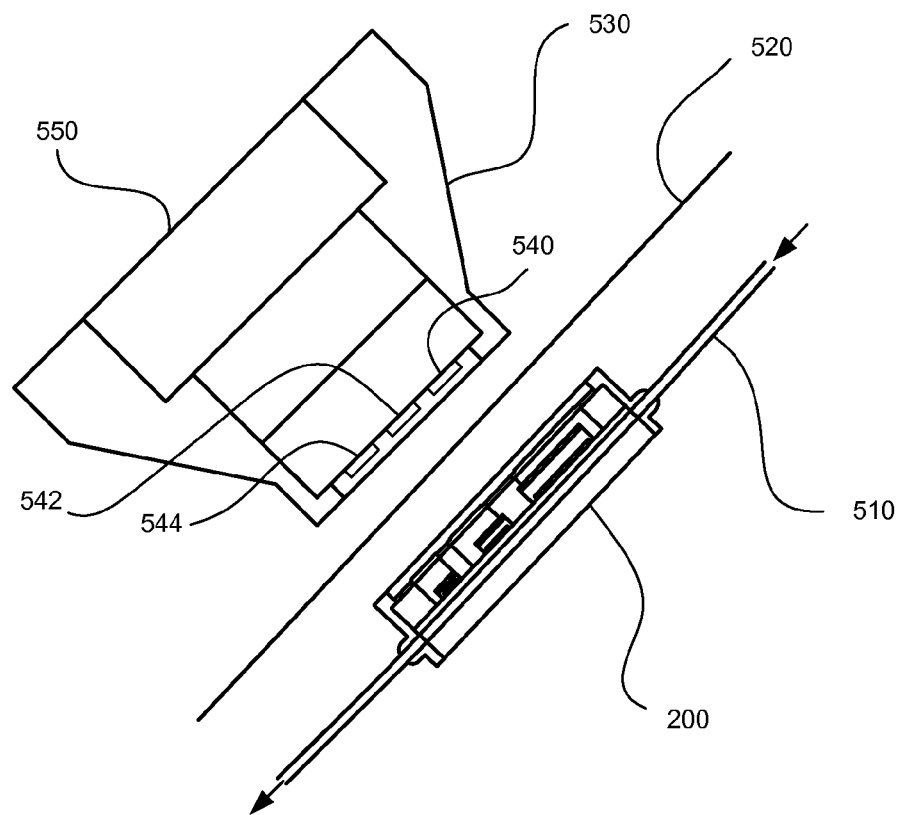
FIG. 5 is a cutaway side view of an exemplary implanted meter and an external reading device according to aspects of the invention.

As shown in FIG. 5, a meter, such as meter 200 show in FIGS. 2 and 3, may be connected with a shunt 510, and fully implanted under the skin 520 of a patient. The combination of the meter 200 and shunt 510 may be configured as a fully implantable unit, for use in-vivo without physical connection to an external device. The meter 200 may be, for example, tunneled surgically under the scalp of a patient, together with a CSF drainage shunt. As described further herein, the meter 200 may have embedded inductor coils, which connected to a capacitor whose properties depend on internal pressure and/or flow conditions.

An external remote reader 530 may be placed in proximity to the meter 200 and inductively couple to the meter through the skin 520 of the patient. For example, individual resonator circuits 540, 542 and 544 may detect changes in inductance of LC circuits of the meter 200. The reader may be configured, for example, to measure shifts in the resonance of the meter's LC circuits, which can then be related to internal pressures and flow rate. Reader 530 may include control circuits and processing logic configured to process the data read into pressure and/or flow information that may be, for example, stored, transmitted via wired or wireless connection and/or displayed for a user on display 550. In embodiments, a reader such as reader 550 may be attached to or included in a garment or other support that allow for the reader to be worn for a prolonged period by a patient, e.g. to allow sustained or periodic remote reading of the pressure and/or flow through meter 200. Further details regarding an exemplary remote reader are shown in FIG. 6.

Figure 6:
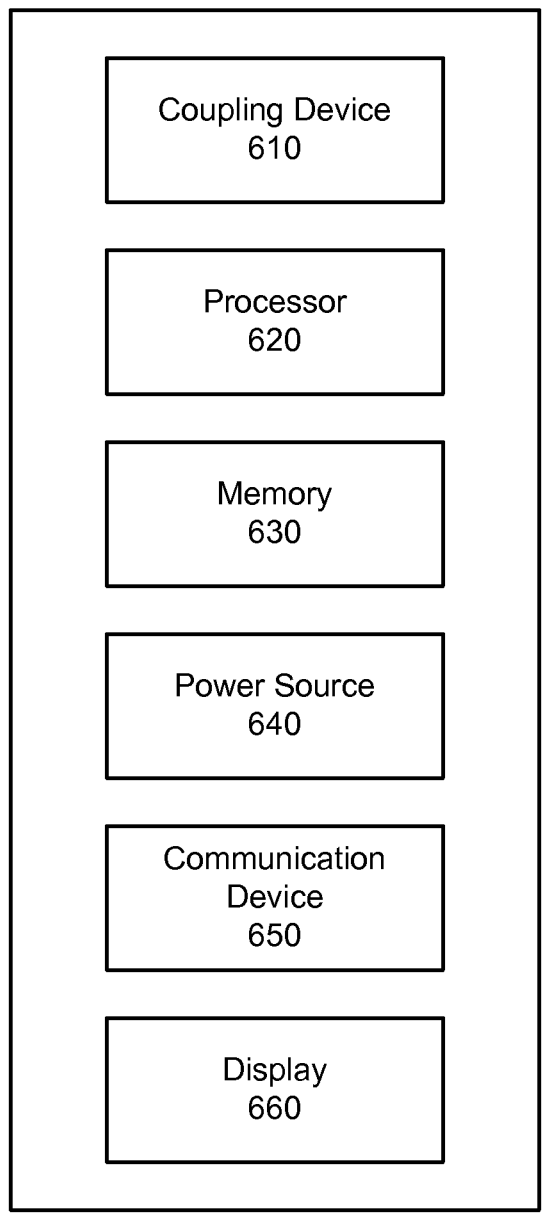
FIG. 6 is a block schematic illustration of an exemplary external reading device according to aspects of the invention.

As shown in FIG. 6, a further embodiment of the invention may include remote reading device 600 with one or more of a coupling device 610, a processor 620, a memory 630, a power source 640, a communication device 650, and/or a display 660. Reading device 600 may be configured to detect changes in capacitance of one or more LC circuits included in an implanted meter as described herein, and may further be configured to communicate with an implanted unit, e.g. by radio transmission and reception, etc. The processor 620 may be configured to process various data detected or received from an implanted meter and/or to store raw and/or processed data in memory 630, or communicate raw, processed and/or stored data to another remote system, e.g. a LAN, smartphone or other handheld device, via communication device 650. Communication device 650 may operate in various modes known in the art, e.g. WiFi, Bluetooth, IR, etc. Memory 630 may include various electronic storage means known in the art. Power source 640 may include various electrical power sources, and may include associated circuitry configured to remotely charge a power source included in an in-vivo implanted device, e.g. by inductive charging.

In embodiments, an external device, such as remote reading device 600, or other microprocessor-drive device with a communication capability, may be configured to remotely control and/or program an implanted device such as device 100 shown in FIG. 1. For example, communication device 650 may be configured to transmit commands, e.g. to adjust flow metering, to stop or start a fluid flow, etc., and/or programming updates to an implanted device.

Figure 7:
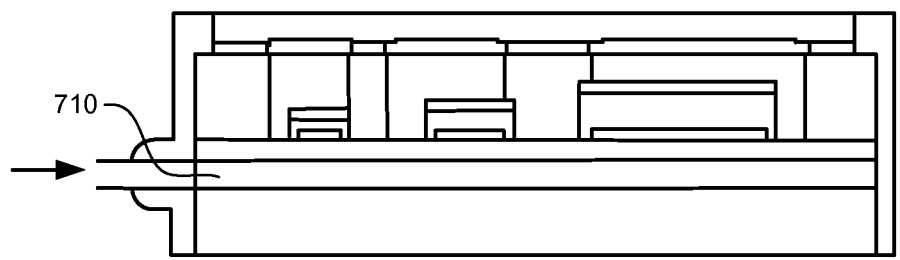
FIG. 7 is a cutaway side view showing details of an exemplary implantable pressure meter according to further aspects of the invention.

According to further aspects of the invention, a meter, similar to meter 200, may be configured to act as a pressure meter, without a flow through the meter. For example, as shown in FIG. 7, a pressure meter 700 may have a microchannel with inlet 710 that is in communication with a vessel. One or more LC circuits such as described above with reference to FIGS. 2 and 3, may be included to detect a pressure within the microchannel. It should be appreciated that a flow meter, such as meter 200, may be configured for use as a pressure meter by blocking an outlet port of the meter, e.g. by closing a valve in the outlet port, and can be transitioned back to use as a flow meter by opening the outlet port. Thus, according to aspects of the invention a single meter may be used, for example, to monitor a non-flow internal pressure, allow flow in response to sensed or other predetermined conditions, monitor a flow rate through the meter, and stop or adjust a flow through the meter.

Figure 8A:
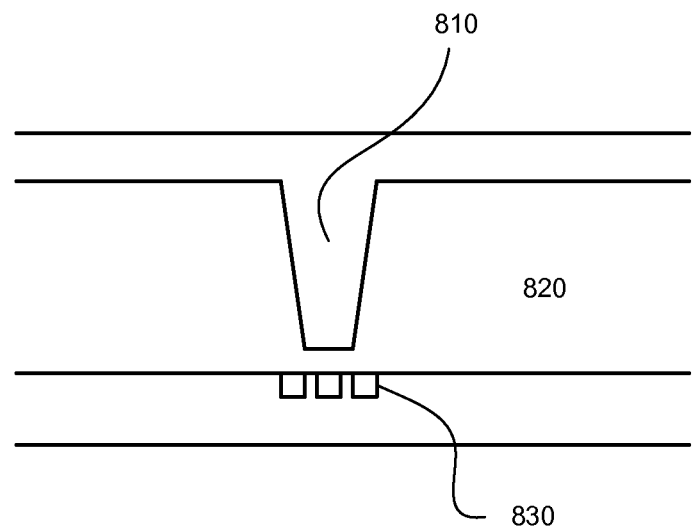
FIGS. 8A-8B are schematic illustrations of an exemplary meter including a dynamic flap according to yet further aspects of the invention.
Figure 8B:
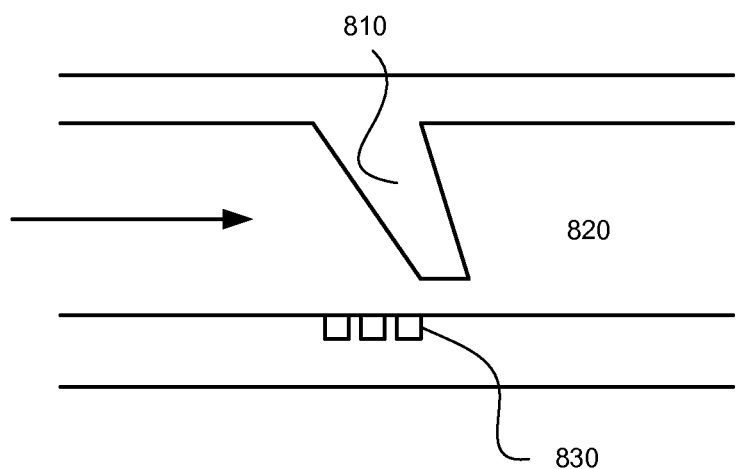

FIGS. 8A and 8B show an alternative approach, which may be used, for example, to measure extremely small flow rates. As shown in FIG. 8A, a flap 810 of a low-dielectric, highly compliant material (e.g., PDMS) may be fabricated into a mircofluidic channel 820 in such a way that it forms part of the dielectric of a capacitor at rest.

Figure 9:
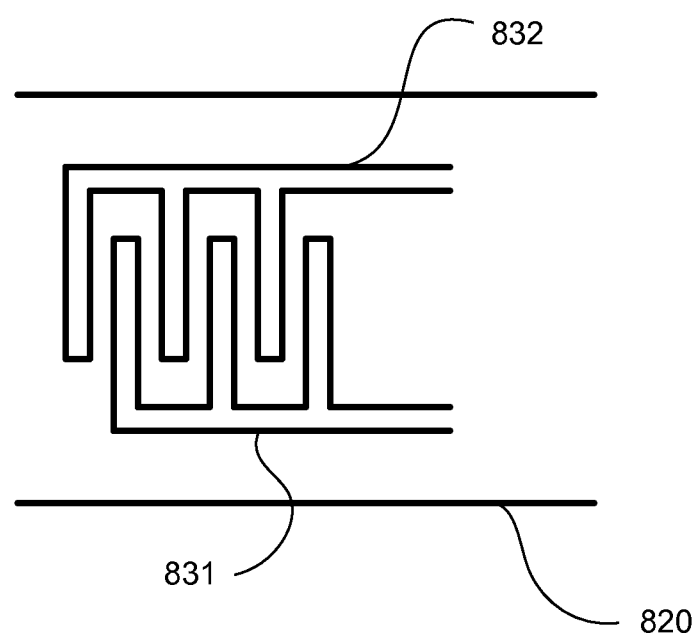
FIG. 9 is a top view of showing additional details of an exemplary interdigitated capacitor which may be used with the dynamic flap shown in FIGS. 8A-8B.

Interdigitated finger capacitor 830 may be disposed on an opposite side of the mircofluidic channel 820. As shown in FIG. 8B, flow of the liquid in the channel (shown by the arrow) may push the flap 810 outside of the capacitor's electric field, replacing it with aqueous medium in the channel. Due to the much higher dielectric constant of water (about 80), this leads to a pronounced drop in capacitance. This drop may be measured using a similar approach to that described above, by integrating the capacitor into a resonant LC circuit, whose resonance frequency can be measured remotely by cross-inductance. A top view of an exemplary interdigitated finger capacitor 830 is shown in FIG. 9, with electrodes 831 and 832 disposed on the bottom of channel 820.

In embodiments, the ultimate performance of exemplary devices may be dictated by the shift in resonance of an LC circuit. Small changes in pressure must lead to detectable changes in frequency. For typical capacitor dimensions in the millimeter-size range, the baseline capacitance at zero pressure may be approximately 10 pF. It has been found that even slight line pressures may push the deformable film upwards, increasing the capacitance quickly. When the pressure is sufficient to close the gap, the capacitance is dictated by the minimum gap size, taken here to be 100 nm (corresponding to a 100 nm thick dielectric layer coating the upper electrode. Assuming an inductor of approximately 50 nH, the resonant frequencies at zero pressure are in the range of 50-200 MHz. This drops as the internal pressure increases, as the capacitance increases due to decreasing the gap size.

According to aspects of the invention, the inventors have produced LC resonators with frequencies in the range of 10-800 MHz range and quality factors (Q) of approximately 50. A reasonable threshold for detection is a frequency shift that is 10% of the resonance bandwidth, corresponding to relative frequency changes of approximately 0.5% of the resonant frequency at Q=20. As such, resolving pressure changes in the 10-300 Pa range may be achieved. In embodiments, to determine flow rate, the pressure change between two sensors at different points along the flow channel may be measured, and the pressure change can be related to flow rate using viscous-loss models for flow in the channel using conventional techniques. The use of different upstream and downstream sensors also presents opportunities for redundant (cross-check) measurements.

As described herein, an aspect of an embodiment of the present invention comprises, but not limited thereto, the integration of microfabricated features into CSF shunt catheter implants both upstream and downstream to the shunt valve that deform in response to CSF pressure.

The description given above is merely illustrative and is not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments.

What is claimed is:

1. An apparatus for use in monitoring treatment of hydrocephalus, comprising:
an implantable shunt;
a meter including one or more microfluidic channels connected to the shunt and configured to detect at least one of pressure and fluid flow rate through the shunt and to be read out remotely by a wirelessly coupled external device,
the meter further includes a plurality of volumetric reservoirs in fluid communication with the one or more microfluidic channels, each of the plurality of reservoirs having different dimensions and configured as separate passive resonant tank (LC) circuits.

2. The apparatus of claim 1, wherein the meter further includes a dynamic layer in communication with the at least one reservoir and a static layer opposite the dynamic layer, the static layer including an inductor coil configured to react to displacement of the dynamic layer.

3. The apparatus of claim 1, wherein the microfluidic channel includes at least one dynamic flap at least partially obstructing the microfluidic channel, the meter configured such that a displacement of the flap changes or modulates a capacitance of a capacitor of the LC circuit.

4. The apparatus of claim 3, the at least one flap comprising a low-dielectric material.

5. The apparatus of claim 3, the at least one flap comprising a membrane of Polydimethylsiloxane (PDMS).

6. The apparatus of claim 1, further comprising an external device configured to inductively couple remotely to at least one of the LC circuits, without physical connections to the implantable shunt or meter, and to display a pressure acting on, or a flow rate of a fluid passing through, the meter.

7. The apparatus of claim 1, wherein the implantable shunt and meter are included in a fully implantable unit, the apparatus further comprising:
a control circuit included in the implantable unit and configured to process data from the meter; and
a memory device included in the implantable unit and configured to store and retrieve the processed data from the control circuit.

8. The apparatus of claim 1, wherein the microfluidic channel includes a plurality of volumetric reservoirs, each of the plurality of reservoirs having different dimensions.

9. The apparatus of claim 8, further comprising a control circuit configured to process data from the meter and to determine a flow rate through the microfluidic channel based at least in part on a pressure differential between the reservoirs.

10. A method of monitoring the treatment of hydrocephalus, comprising:

implanting a shunt including a meter with a microfluidic channel into a patient;

detecting at least one of a pressure acting on, and a flow rate of a fluid through, the shunt via an LC circuit included in the meter; and communicating information regarding the detected pressure and/or flow rate to an external device via inductive coupling and without physical connection of the external device to the shunt or the flow meter, wherein the meter includes a plurality of volumetric reservoirs, each of the plurality of reservoirs having different dimensions and configured as separately readable LC circuits.

11. The method of claim 10, wherein the microfluidic channel includes at least one volumetric reservoir.

12. The method of claim 11, wherein the meter further includes a dynamic layer in communication with the at least one reservoir and a static layer opposite the dynamic layer, the static layer including an inductor coil configured to react to displacement of the dynamic layer.

13. The method of claim 10, wherein the microfluidic channel includes at least one dynamic flap at least partially obstructing the microfluidic channel, the flow meter configured such that a displacement of the flap changes a capacitance of a capacitor of the LC circuit.

* * * * *